United States Patent [19]
Howard, III et al.

[11] Patent Number: 5,928,227
[45] Date of Patent: Jul. 27, 1999

[54] REMOTE CONTROLLED COAGULATOR SYSTEM AND METHODS

[75] Inventors: Matthew A. Howard, III; Bruce Abkes; Roman Mirsky, all of Iowa City, Iowa

[73] Assignee: The University of Iowa Research, Iowa City, Iowa

[21] Appl. No.: 08/827,996

[22] Filed: Mar. 10, 1997

[51] Int. Cl.⁶ .................................................. A61B 17/36
[52] U.S. Cl. ............................................. 606/40; 341/176
[58] Field of Search .................................. 606/1, 32, 33, 606/34, 37, 40; 341/176; 137/870, 884; 340/825.69, 825.71, 825.72, 825.76

[56] References Cited

U.S. PATENT DOCUMENTS

| | | | |
|---|---|---|---|
| 3,875,945 | 4/1975 | Friedman . | |
| 4,492,231 | 1/1985 | Auth | 128/303.17 |
| 4,548,207 | 10/1985 | Reimels | 128/303.17 |
| 4,590,934 | 5/1986 | Malis et al. | 128/303.14 |
| 4,674,499 | 6/1987 | Pao | 128/303.14 |
| 4,809,117 | 2/1989 | Friedman . | |
| 5,089,002 | 2/1992 | Kirwan, Jr. | 606/50 |
| 5,091,656 | 2/1992 | Gahn . | |
| 5,173,778 | 12/1992 | Sasaki et al. . | |
| 5,249,121 | 9/1993 | Baum et al. | 364/413.01 |

*Primary Examiner*—George Manuel
*Attorney, Agent, or Firm*—Fleshner & Kim

[57] ABSTRACT

A remote control system and method for remotely controlling a supply of electrical power to an electrically powered device, the system comprising transmitting means for transmitting electromagnetic radiation, receiving means for receiving electromagnetic radiation, and first and second switching means. The remote control system and method provides for the hands-free operation of such an electrically powered device while allowing the operator the freedom of mobility in spatial relationship to the electrically powered device.

57 Claims, 8 Drawing Sheets

REMOTE CONTROLLED COAGULATOR SYSTEM AND METHODS

BACKGROUND OF THE INVENTION

1. Field of the Invention

The present invention relates generally to a remote control system, to a method for controlling a supply of electrical power to an electrically powered device, and to a method of making a remote controlled system including an electrically powered device. The present invention also relates to a remote control system and method for controlling a surgical instrument. In particular, the present invention relates to a remote controlled coagulator system, to a method for controlling the same, and to a method of making the same. More particularly, the present invention relates to a remote controlled, foot-activated coagulator system and method which allows a surgeon to conveniently control the coagulator from any location in the vicinity of the operating table during the course of a surgical procedure.

2. Background of the Related Art

Coagulators, such as bipolar coagulators, are surgical instruments which are commonly used in a broad range of surgical procedures for selectively electro-coagulating blood or electro-cauterizing tissue. Most coagulators in use today are of the bipolar type and comprise a pair of electrodes of opposite polarity, arranged either coaxially or on opposing arms of a forceps-like instrument. Bipolar coagulators are widely used by almost all surgical specialists. For example, bipolar coagulators are commonly used in surgical procedures to the eyes, nose, and other features of the face and cranium.

Currently used or prior art bipolar coagulators and coagulator systems have the disadvantage that they are controlled by a foot pedal device which is attached or tethered to a coagulator control box of the coagulator system via an electrical cable. Again, prior art coagulator systems require the surgeon or the operator of the system to apply mechanical pressure to the foot pedal in order to actuate the coagulator. Therefore, to be able to control or actuate a prior art coagulator it is necessary for the surgeon to remain in a more or less fixed physical relationship with respect to the coagulator foot pedal control; i.e. the surgeon must remain in approximately the same location.

The remote controlled coagulator system of the instant invention eliminates the requirement, exhibited by prior art coagulators, for the surgeon or a member of the surgical team to search for, and reposition, the coagulator foot pedal as the surgeon moves to different positions around the operating room table during a surgical procedure.

U.S. Pat. No. 4,492,231 to Auth discloses a bipolar electro-coagulation system in which the arms of the forceps are of a material having a high thermal conductivity in order to prevent excessive heat build up in the arms of the forceps. The coagulator is connected to a radiofrequency generator for supplying power to the electrodes of the coagulator, and the radiofrequency coagulator is actuable by either a conventional foot operated switch, or by a switch built into the forceps portion of the system. In the case of the built-in switch, the switch is turned on and the radiofrequency generator activated when the arms of the forceps are squeezed together beyond a certain pre-set position.

U.S. Pat. No. 4,590,934 to Malis et al. discloses a bipolar cutter/coagulator which is controlled by a foot pedal interface. It is operated in the cut mode and the coagulate mode by depressing the cut pedal contact arm and the coagulate pedal contact arm, respectively, i.e. each mode (cut and coagulate) is operated by a separate foot pedal switch.

U.S. Pat. No. 5,091,656 to Gahn discloses a foot pedal switch apparatus for "remotely" controlling surgical instruments. The foot switch assembly is linked directly or tethered to the system console by a length of multiconductor electrical cable.

U.S. Pat. No. 5,249,121 to Baum et al. discloses a "remote" control unit for an ophthalmic surgical system. However, the "remote" controller is connected or tethered to the main console of the system via an electrical umbilical cord.

In contrast, the remote controlled coagulator system of the instant invention allows the surgeon to remotely control the coagulator from any location around the operating room table, while at the same time the surgeon's hands remain free for performing other functions. The remote controlled actuating system of the instant invention comprises a control means which is not attached or tethered to the coagulator control box, and allows the surgeon to freely change positions as dictated by various surgical procedures while retaining convenient access to the coagulator power switch at all times, as will be described fully hereinbelow.

SUMMARY OF THE INVENTION

Accordingly, one object of the present invention is to provide a remote control system for remotely controlling supply of electrical power to an electrically powered device by an operator.

It is another object of the present invention to provide a remote control system for remotely controlling supply of electrical power to a surgical instrument, such as a bipolar coagulator.

It is another object of the invention to provide a remote control system for controlling the supply of electrical power to an electrically powered device, the remote control system comprising: transmitting means for transmitting electromagnetic radiation, receiving means for receiving electromagnetic radiation, first switching means for turning on or off a supply of electrical power, and second switching means for interchanging the first switching means between an active state and an inactive state.

It is another object of the invention to provide a remote control system for controlling the supply of electrical power to an electrically powered device, the remote control system comprising: infrared transmitting means for transmitting infrared radiation, infrared receiving means for receiving infrared radiation, first switching means for turning on or off a supply of electrical power, and second switching means for interchanging the first switching means between an active state and an inactive state.

It is another object of the present invention to provide a remote controlled bipolar coagulator system comprising a bipolar coagulator and a bipolar coagulator control box, wherein the supply of electrical power to the bipolar coagulator control box and the bipolar coagulator is controlled by a foot-pressure power switch which is attached to a first surgeon's shoe to be worn by an operator of the remote controlled bipolar coagulator system, and wherein the foot-pressure power switch is not attached, tethered, or directly connected to either the bipolar coagulator or the bipolar coagulator control box.

It is another object of the present invention to provide a convenient method for remote control of an electrical device by an operator in a hands-free fashion by means of a plurality of foot-operated switching means.

It is another object of the invention to provide a method for remote control of a bipolar coagulator of a bipolar coagulator system in a hands-free fashion by means of a foot-operated switch which is not attached to or physically connected to the bipolar coagulator or the bipolar coagulator control box.

It is another object of the invention to provide a method for remote control of a bipolar coagulator of a bipolar coagulator system in a hands-free fashion by means of a foot-operated switch which is attached to the sole of a first shoe to be worn by the operator, wherein the foot-operated switch is not hard-wired to any component outside the shoe.

It is another object of the invention to provide a method of making a remote controlled bipolar coagulator system, wherein the system comprises a transmitter for transmitting electromagnetic radiation, a power switch, and a magnetic activation switch.

It is another object of the invention to provide a method of making a remote controlled bipolar coagulator system, wherein the method comprises attaching the transmitter for transmitting electromagnetic radiation, the power switch, and the magnetic activation switch to a first shoe to be worn by an operator of the remote controlled bipolar coagulator system.

It is another object of the invention to provide a method of making a remote controlled bipolar coagulator system, wherein the method comprises providing a bipolar coagulator control box having a receiver for receiving electromagnetic radiation transmitted from a transmitter, the transmitter attached to a first shoe to be worn by an operator of the remote controlled bipolar coagulator system.

It is another object of the invention to provide a method of making a remote controlled bipolar coagulator system, wherein the method comprises: attaching a power switch, a magnetic activation switch, and a transmitter to a first shoe to be worn by an operator of the remote controlled bipolar coagulator system, and attaching magnetic means to a second shoe to be worn by an operator of the remote controlled bipolar coagulator system.

One advantage of the present invention is that a supply of electrical power to an electrically powered device can be controlled by means of a foot-pressure power switch.

Another advantage of the invention is that a supply of electrical power to an electrically powered device can be controlled by means of a foot-pressure power switch, wherein the foot-pressure power switch is not attached to, connected to, or tethered to the electrically powered device.

Another advantage of the invention is that the foot-pressure power switch for controlling the supply of electrical power to an electrically powered device can be interchanged between an active state and an inactive state by means of a magnetic activation switch.

Another advantage of the invention is that the magnetic activation switch for interchanging the foot-pressure power switch between an active state and an inactive state can be controlled by movement of at least one of the operator's feet.

Another advantage of the invention is that it provides a method for remote control of an electrical device by an operator in a hands-free fashion by means of a foot operated remote control system.

Another advantage of the invention is that it provides a method for remote control of a bipolar coagulator system solely by appropriate movement of the operator's feet.

Another advantage of the invention is that it provides a method for remote control of a bipolar coagulator system wherein a surgeon is free to move to any position around the operating room table while retaining the ability to control the bipolar coagulator.

One feature of the invention is that it allows the hands-free control of the supply of electrical power to an electrically powered device by the operator of the electrically powered device.

Another feature of the invention is that it includes a remote control system for controlling the supply of electrical power to an electrically powered device, the remote control system comprising: transmitting means for transmitting electromagnetic radiation, receiving means for receiving electromagnetic radiation, first switching means for turning on or off a supply of electrical power, and second switching means for interchanging the first switching means between an active state and an inactive state.

Another feature of the invention is that the first switching means comprises a foot-pressure power switch attached to a first shoe to be worn by the operator of the electrically powered device.

Another feature of the invention is that the second switching means comprises a magnetic activation switch.

Another feature of the invention is that the magnetic activation switch comprises a plurality of magnetic detectors arranged at separate locations on the first shoe to be worn by the operator of the electrically powered device.

Another feature of the invention is that the magnetic activation switch is controlled by means of a magnetic means attached to a second shoe to be worn by the operator of the electrically powered device.

Another feature of the invention is that it provides a remote controlled surgical coagulator system, comprising: at least one electrode coupled to a supply of electrical power; a coagulator control box; a receiver coupled to the coagulator control box, the receiver for receiving electromagnetic radiation; transmitting means for transmitting electromagnetic radiation, wherein the transmitting means is mobile and untethered to the coagulator control box; first switching means, wherein the first switching means is also mobile and untethered to the coagulator control box; and second switching means, wherein the second switching means is also mobile and untethered to the coagulator control box.

Another feature of the invention is that it provides a remote controlled surgical coagulator system, comprising at least one electrode, a coagulator control box, and a power switch for turning on or turning off a supply of electrical power to the coagulator control box.

Another feature of the invention is that it provides a remote controlled surgical coagulator system, comprising a foot-pressure power switch for turning on or turning off a supply of electrical power to the coagulator control box.

Another feature of the invention is that it provides a remote controlled, electrically powered medical device, comprising a magnetic activation switch for interchanging the power switch between an active state and an inactive state.

Another feature of the invention is that it provides a remote controlled surgical coagulator system, comprising a magnetic activation switch for interchanging the power switch between an active state and an inactive state.

Another feature of the invention is that it provides a convenient method for remote control of an electrically powered device by an operator of the electrically powered device in a hands-free fashion by means of a plurality of foot-operated switching means.

Another feature of the invention is that it provides a method for remote control of a bipolar coagulator of a remote controlled bipolar coagulator system in a hands-free fashion by means of a foot-pressure power switch.

Another feature of the invention is that it provides a method for remote control of a surgical fluoroscope of a remote controlled surgical fluoroscope system in a hands-free fashion by means of a foot-pressure power switch.

These and other objects, advantages, and features of the invention are accomplished by the provision of a remote control system for remotely controlling supply of electrical power to an electrically powered device by an operator of the electrically powered device, the system comprising: transmitting means for transmitting electromagnetic radiation; receiving means for receiving electromagnetic radiation; first switching means attached to a first shoe to be worn by the operator; and second switching means attached to the first shoe to be worn by the operator.

These and other objects, advantages, and features of the invention are accomplished by the provision of a remote control system for remotely controlling supply of electrical power to an electrically powered device by an operator of the electrically powered device, the system comprising: infrared transmitting means for transmitting infrared radiation; infrared receiving means for receiving infrared radiation; first switching means attached to a first shoe to be worn by the operator; and second switching means attached to the first shoe to be worn by the operator.

These and other objects, advantages, and features of the invention are accomplished by the provision of a remote controlled coagulator system including a bipolar coagulator for use by a surgeon in performing surgical procedures, the remote controlled coagulator system comprising: a coagulator control box coupled to a supply of electrical power; receiving means for receiving electromagnetic radiation; transmitting means for transmitting electromagnetic radiation; first switching means; and second switching means, wherein said transmitting means, said first switching means, and said second switching means are mobile and unattached to both said coagulator control box and to said bipolar coagulator.

These and other objects, advantages, and features of the invention are accomplished by the provision of a method of turning on or turning off electrical power to an electrically powered device, the method comprising the steps of: moving a magnetic means in close proximity to a second magnetic detector so that a power switch is changed from an inactive state to an active state; applying foot pressure to the power switch so that the power switch is switched to the on mode; after a requisite period of time, reapplying foot pressure to the power switch so that the power switch is switched to the off mode; and thereafter, moving the magnetic means in close proximity to a first magnetic detector so that the power switch is changed from the active state to the inactive state.

These and other objects, advantages, and features of the invention are accomplished by the provision of a method for controlling a bipolar coagulator during a surgical procedure using a remote control system, said method comprising the steps of: moving a magnetic means in close proximity to a second magnetic detector so that a power switch is changed from an inactive state to an active state; applying foot pressure to the power switch so that the power switch is switched to an on mode; thereafter, operating the bipolar coagulator for a period of time commensurate with the surgical procedure; thereafter, reapplying foot pressure to the power switch so that the power switch is switched to the off mode; and thereafter, moving the magnetic means in close proximity to a first magnetic detector so that the power switch is changed from the active state to the inactive state.

These and other objects, advantages, and features of the invention are accomplished by the provision of a method of making a remote controlled system including an electrically powered device, said method comprising the steps of: attaching a power switch to a first shoe to be worn by an operator of the electrically powered device; further attaching a magnetic activation switch to the first shoe to be worn by the operator of the electrically powered device; further attaching an infrared or radiofrequency transmitter to the first shoe to be worn by the operator of the electrically powered device; electrically coupling the power switch, the magnetic activation switch, and the infrared or radiofrequency transmitter; attaching magnetic means to a second shoe to be worn by the operator of the electrically powered device; and, coupling an infrared or radiofrequency receiver to the electrically powered device.

Additional objects, advantages, and features of the invention will in part be set forth in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements except as indicated, wherein.

DETAILED DESCRIPTION OF PREFERRED EMBODIMENTS

A remote control system for controlling the supply of electrical power to an electrically powered device according to the instant invention comprises transmitting means for transmitting electromagnetic radiation; receiving means for receiving electromagnetic radiation; and first and second switching means, wherein both first and second switching means are attached to a first shoe to be worn by the operator of the electrically powered device. The preferred embodiments of a remote control system and method for hands-free control of an electrically powered device, such as a remote controlled surgical coagulator system, will now be described with reference to the accompanying drawings.

Figure 1:
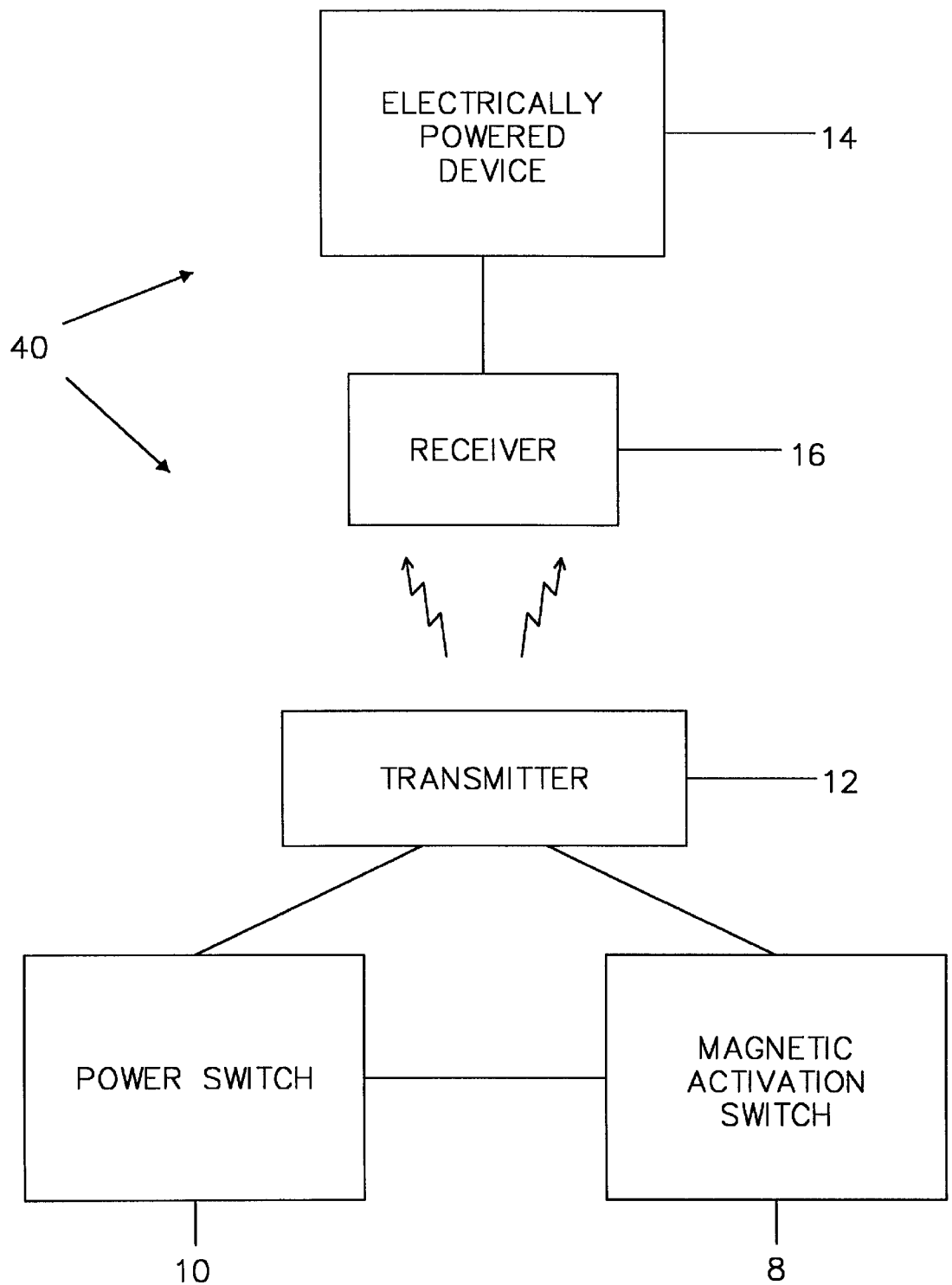
FIG. 1 shows a remote control system for controlling the supply of electrical power to an electrically powered device according to one embodiment of the invention.

FIG. 1 shows a schematic representation of a remote control system 40 according to the present invention. A magnetic activation switch 8 is electrically coupled to a power switch 10. Both power switch 10 and magnetic activation switch 8 are electrically coupled to a transmitting means such as a transmitter 12. Power switch 10, magnetic activation switch 8, and transmitter 12 are all attached to a first shoe to be worn by an operator of an electrically powered device 14.

Transmitter 12 is capable of transmitting electromagnetic radiation, and transmitter 12 can be a transmitter which transmits electromagnetic radiation in the radiofrequency range, in the infrared range, or in other wavelength ranges. According to a preferred embodiment of the invention, transmitter 12 is a transmitter which transmits electromagnetic radiation in the infrared range. A receiving means such as receiver 16 is coupled to an electrically powered device 14 in such a manner so that power to electrically powered device 14 is turned on when receiver 16 receives electromagnetic radiation of a pre-defined wavelength or wavelength range. By analogy with transmitter 12, receiver 16 can be a receiver which transmits electromagnetic radiation in the radiofrequency range, in the infrared range, or in other wavelength ranges. According to a preferred embodiment of the invention, receiver 16 is a receiver which receives electromagnetic radiation in the infrared range. Receiver 16 is coupled to electrically powered device 14 in such a manner that electrical power is supplied to electrically powered device 14 when receiver 16 receives electromagnetic radiation of a given wavelength or wavelength range.

What has been stated above regarding the nature of transmitter 12 and receiver 16 in the context of remote control system 40 equally applies to other embodiments of the invention, including systems 50 and 60 described hereinbelow.

Again with reference to FIG. 1, magnetic activation switch 8 can interchange power switch 10 between an active state and an inactive state by means of a magnetic unit 22 (not shown in FIG. 1) which is manipulated by an operator of remote control system 40. When power switch 10 is in the active state, power switch 10 can be switched to the on mode, thereby closing an electrical circuit (not shown) and initiating transmission of electromagnetic radiation from transmitter 12. Receiver 16 receives electromagnetic radiation transmitted from transmitter 12 and power is turned on to electrically powered device 14.

While power switch 10 is in the active state, the supply of electrical power to electrically powered device 14 can be turned off by switching power switch 10 to the off mode. Under these circumstances, transmitter 12 no longer transmits electromagnetic radiation, receiver 16 no longer receives electromagnetic radiation from transmitter 12, and electrical power to electrically powered device 14 is turned off.

When power switch 10 is changed to the inactive state (deactivated), power switch 10 is inoperable, i.e., it will not initiate transmission of electromagnetic radiation from transmitter 12, and it will not allow electrically powered device 14 to be turned on no matter how many times power switch 10 is switched between the on mode and the off mode.

Power switch 10, magnetic activation switch 8, and transmitter 12 are attached to a first shoe 20 (FIG. 2) to be worn by the operator of electrically powered device 14. Magnetic unit 22 (FIG. 3) is attached to a second shoe 21 (also FIG. 3) to be worn by the operator of electrically powered device 14.

Figure 2:
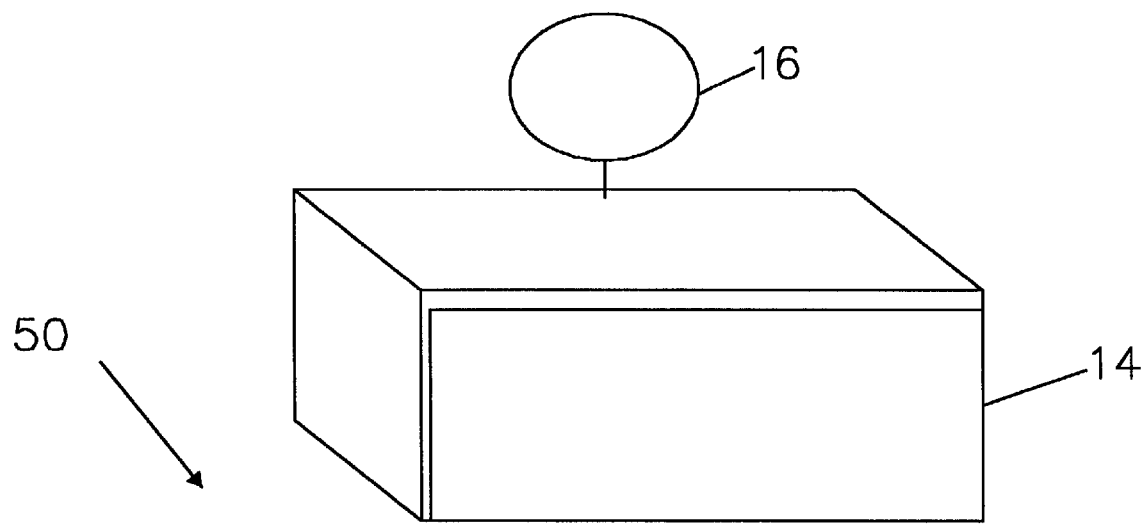
FIG. 2 shows a remote control system for controlling the supply of electrical power to an electrically powered device according to another embodiment of the invention.
Figure 2:
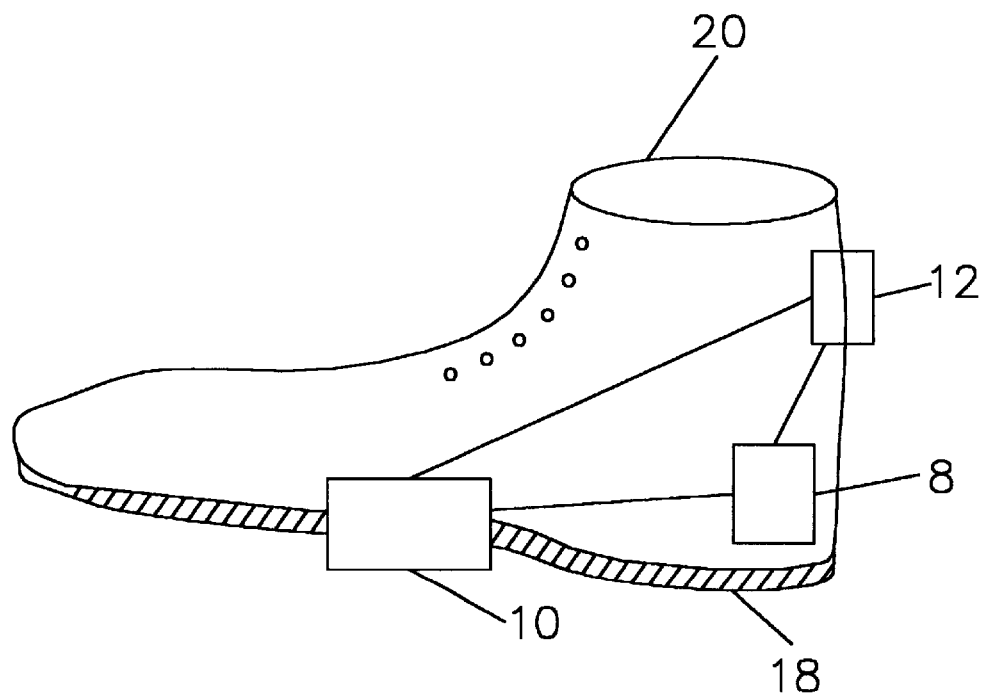

According to another embodiment of the invention as shown in FIG. 2, magnetic activation switch 8 is attached to first shoe 20 and is located near the heel area of first shoe 20. Magnetic activation switch 8 is electrically coupled to power switch 10, and the former has the ability to interchange the activation status of the latter between a first (active) state and a second (inactive) state. Power switch 10 is arranged on the sole 18 of first shoe 20, and an example of power switch 10 is a foot-pressure switch which is switched between the on mode and the off mode by the application of sufficient force or pressure. In a preferred embodiment, sufficient pressure may be applied to actuate power switch 10 simply by tapping or pressing sole 18 of first shoe 20 against the floor. Power switch 10 acts as a "toggle" switch and switches between on mode and off mode each time sufficient pressure is applied to power switch 10.

Transmitter 12 is also attached to first shoe 20, is electrically coupled to both power switch 10 and magnetic activation switch 8, and transmits electromagnetic radiation when activated by power switch 10. That is to say, when power switch 10 is in the active state and is turned to the on, transmitter 12 transmits electromagnetic radiation. Electromagnetic radiation transmitted from transmitter 12 is received by receiver 16, the latter being electrically coupled to electrically powered device 14 such that when receiver 16 receives electromagnetic radiation of a predefined wavelength range, electrical power is supplied to electrically powered device 14.

Figure 3:
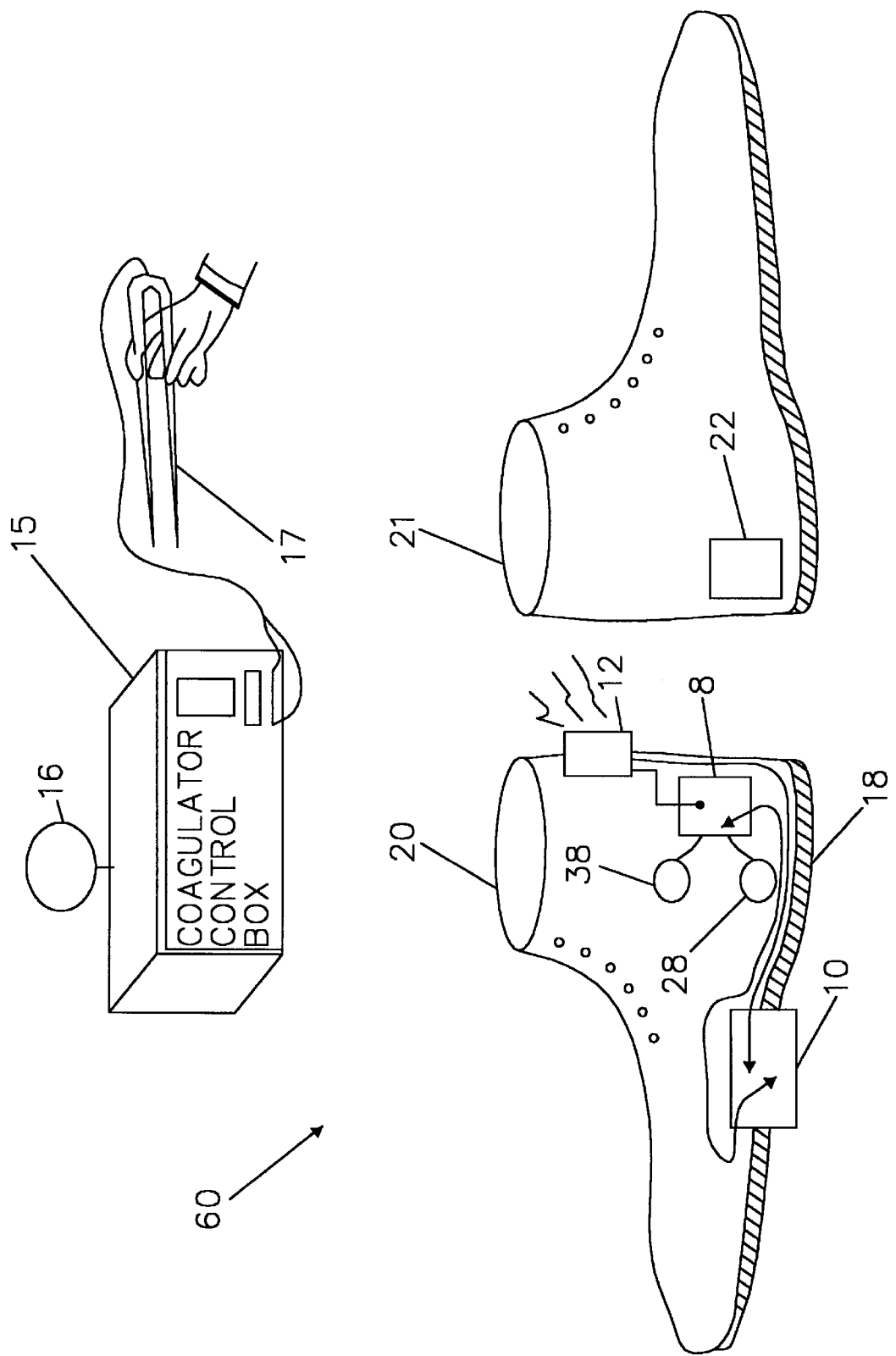
FIG. 3 shows a remote controlled bipolar coagulator system according to another embodiment of the invention.

In another embodiment, the invention includes a remote controlled bipolar coagulator system, wherein magnetic activation switch 8, power switch 10, and transmitter 12 are electrically coupled to each other and attached to first shoe 20 substantially according to the arrangement shown in FIG. 3. Thus, power switch 10 is attached to sole 18, magnetic activation switch 8 is located in the heel area, and transmitter 12 is located above magnetic activation switch 8. Power switch 10 can again be a foot-pressure switch which is actuated, for example, by the application of pressure to the switch by pressing the foot which bears first shoe 20 against the floor. Preferably, power switch 10 is actuated (interchanged between on mode and off mode) simply by tapping the sole of the foot against the floor.

Again with reference to FIG. 3, magnetic unit 22 is attached to second shoe 21. Magnetic unit 22 may be located at various positions on or within second shoe 21. However in a preferred embodiment of the invention, magnetic unit 22 is located near the heel area of second shoe 21, and more preferably, magnetic unit 22 is located along the medial aspect of the heel.

Magnetic unit 22 can be, for example, a small permanent bar magnet. Magnetic activation switch 8 may comprise first and second magnetic detectors (or magnetic sensors) 28 and 38, respectively.

In a preferred embodiment, first and second magnetic sensors 28 and 38 are arranged along the medial aspect of the heel of first shoe 20. When magnetic unit 22 is brought in close proximity to first magnetic detector 28, power switch 10 is changed to the inactive state (deactivated). In this situation, power switch 10 is inoperable, i.e., it will not initiate transmission of electromagnetic radiation from transmitter 12, and it will not allow electrically powered device 14 to be turned on no matter how many times power switch 10 is switched between the on mode and the off mode. Conversely, when magnetic unit 22 is brought in close proximity to second magnetic detector 38, power switch 10 is changed to the active state (activated). In this situation, when power switch 10 is turned on, electromagnetic radiation is transmitted from transmitter 12 to receiver 16 and electrical power is supplied to electrically powered device 14, at which time an electric current from bipolar coagulator 17 may be used for electro-coagulation or electro-cauterization of blood or tissue.

A method of using a remote control system according to the invention to control an electrically powered device, for example, a bipolar coagulator will be described below with reference to the components shown for remote control system 60 in FIG. 3. Remote control system 60 is comprised of bipolar coagulator control box 15 and bipolar coagulator 17, wherein bipolar coagulator 17 can provide electric current in order to electro-coagulate or electro-cauterize blood or tissue during a surgical procedure. With power switch 10 in the inactive state, magnetic unit 22 is first moved in close proximity to second magnetic detector 38 in order to activate power switch 10. Then, foot pressure is applied to power switch 10 in order to switch power switch 10 to the on mode and concomitantly to turn on bipolar coagulator 17 via coagulator control box 15, receiver 16, and transmitter 12. After a requisite period of time, foot pressure is again applied to power switch 10 in order to switch power switch 10 to the off mode and concomitantly to turn off bipolar coagulator 17 via control box 15, receiver 16, and transmitter 12. Next, magnetic unit 22 is moved in close proximity to first magnetic detector 28 in order to deactivate power switch 10. The above series of steps may be repeated as often as necessary during the course of the surgical procedure.

Figure 4:
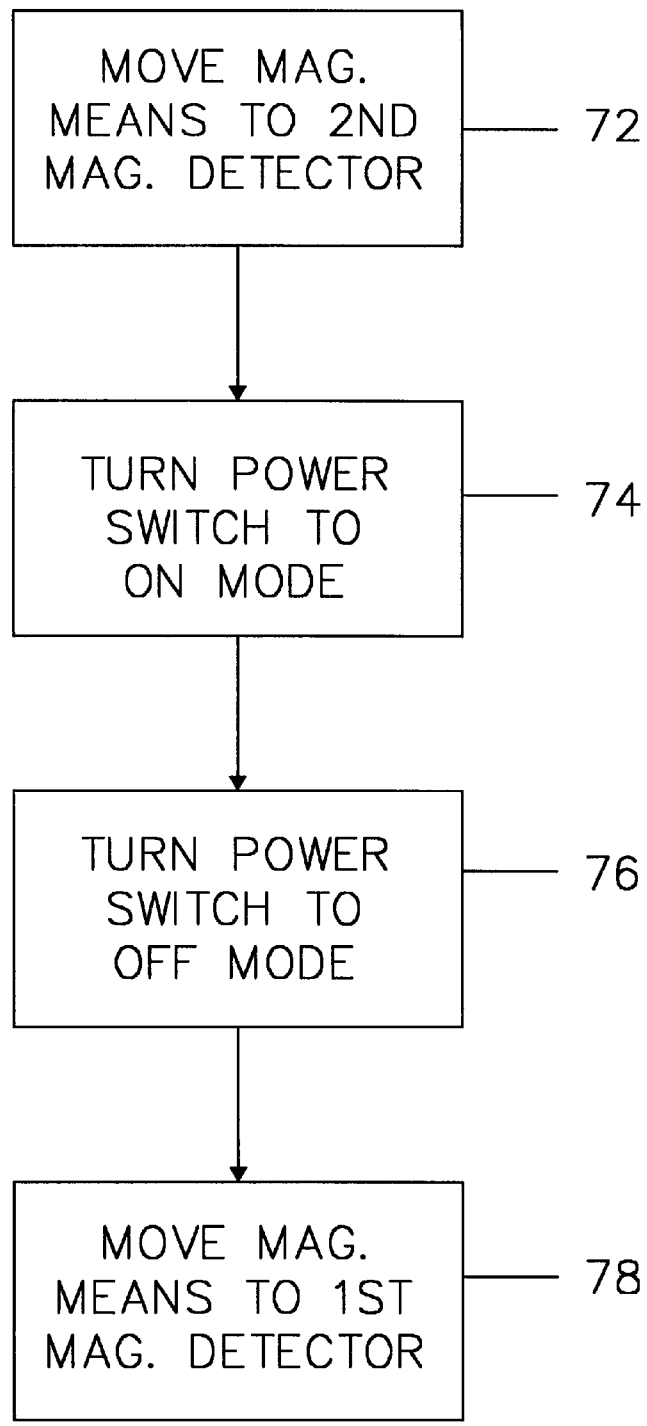
FIG. 4 schematically shows the steps in a method for controlling an electrically powered device according to one embodiment of the invention.

A method for controlling an electrically powered device (not shown in FIG. 4) using the components of a remote control system (also not shown in FIG. 4) according to the invention is schematically represented in FIG. 4, wherein the method comprises the steps of: moving magnetic unit 22 in close proximity to second magnetic detector 38, in step 72, so that power switch 10 is changed from an inactive state to an active state; then, applying foot pressure to power switch 10 so that power switch 10 is in the on mode, in step 74; after a requisite period of time, applying foot pressure to power switch 10 so that power switch 10 is in the off mode, in step 76; and thereafter moving magnetic unit 22 in close proximity to first magnetic detector 28 so that power switch 10 is changed from an active state to an inactive state, in step 78.

Figure 5:
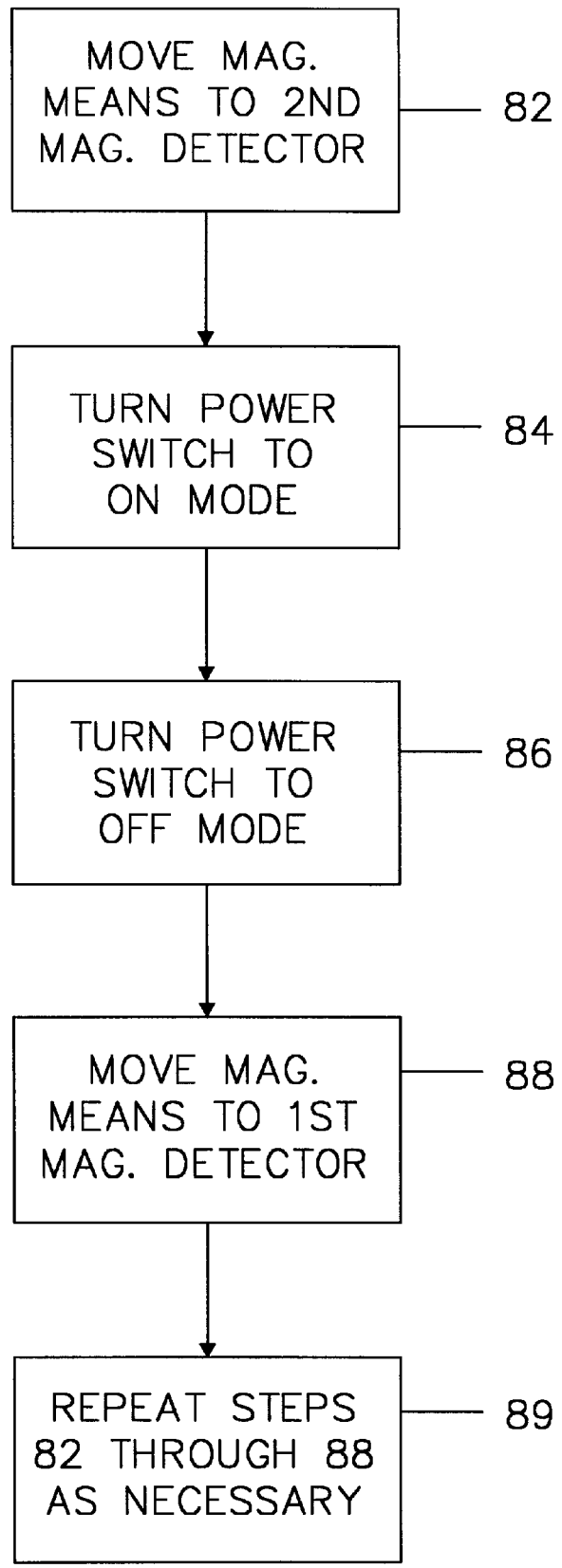
FIG. 5 schematically shows the steps in a method for controlling an electrically powered device according to another embodiment of the invention.

With reference to FIG. 5, a method for controlling an electrically powered device according to another embodiment of the instant invention comprises the steps of: moving magnetic unit 22 in close proximity to second magnetic detector 38, in step 82, so that power switch 10 is changed from an inactive state to an active state; then, applying foot pressure to power switch 10 so that power switch 10 is in the on mode, in step 84; after a requisite period of time, applying foot pressure to power switch 10 so that power switch 10 is in the off mode, in step 86; thereafter moving magnetic unit 22 in close proximity to first magnetic detector 28 so that power switch 10 is changed from an active state to an inactive state, in step 88; and repeating steps 82 through 88 as many times as is deemed necessary, in step 89.

Figure 6:
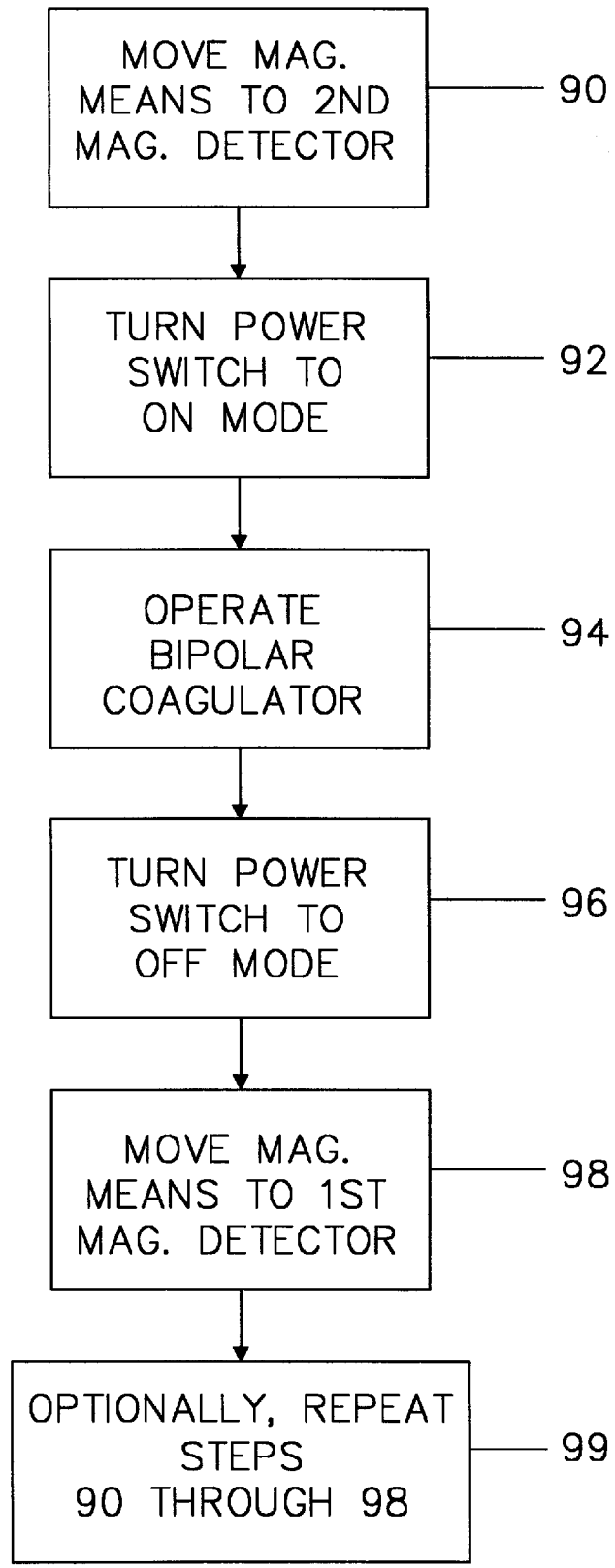
FIG. 6 schematically shows the steps in a method for controlling a remote controlled bipolar coagulator system according to another embodiment of the invention.

A method for controlling a bipolar coagulator of a remote controlled bipolar coagulator system according to another embodiment of the instant invention is shown schematically in FIG. 6, and comprises the steps of: moving magnetic unit 22 in close proximity to second magnetic detector 38, in step 90, so that power switch 10 is changed from an inactive state to an active state; then, applying foot pressure to power switch 10 so that power switch 10 is in the on mode, in step 92; thereafter, operating bipolar coagulator 17 for a period of time commensurate with a given surgical procedure to be undertaken, in step 94; after a requisite period of time, applying foot pressure to power switch 10 so that power switch 10 is switched to the off mode, in step 96; thereafter moving magnetic unit 22 in close proximity to first magnetic detector 28 so that power switch 10 is changed from an active state to an inactive state, in step 98; and, repeating steps 90 through 98, as many times as is deemed necessary, in step 99.

Figure 7A:
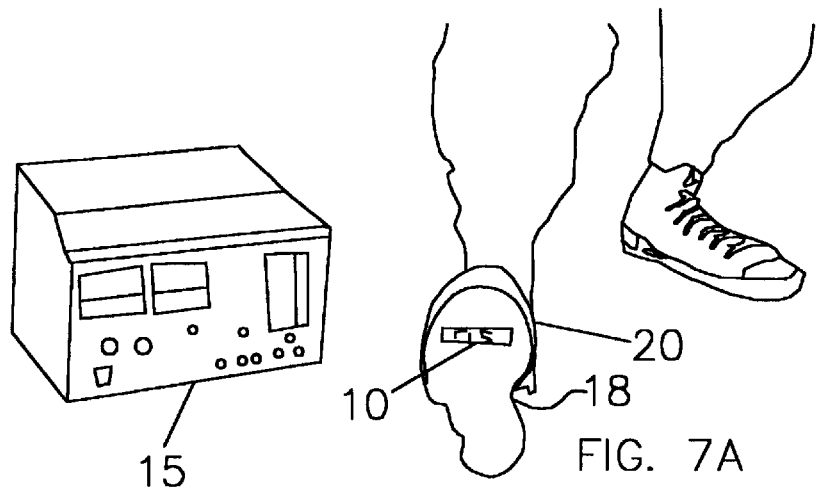
FIG. 7A shows the position of a foot-pressure power switch attached to the sole of a right shoe, according to one embodiment of the invention.

With reference to FIG. 7A, the light colored rectangular area on the sole of a right shoe indicates the approximate location of foot-pressure power switch 10, according to one embodiment of the invention.

Figure 7B:
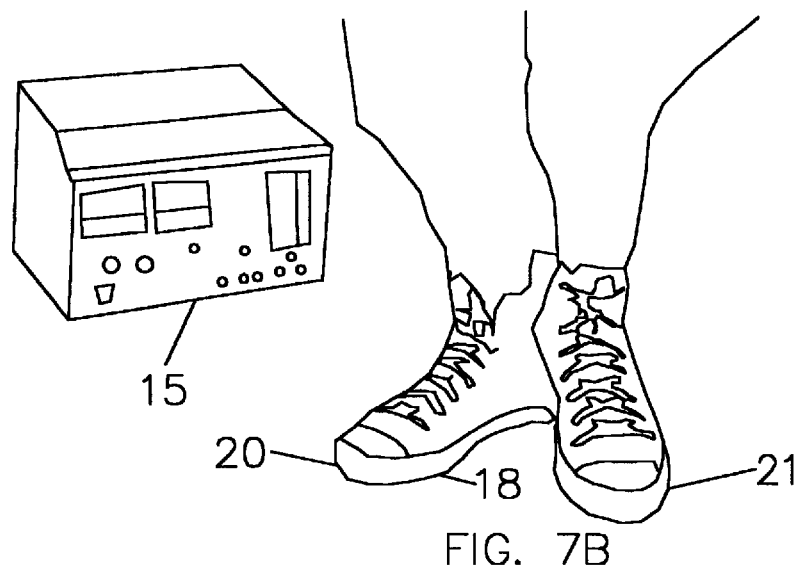
FIG. 7B shows the proximity of the heel of a left (second) shoe, which bears a magnet, to a second magnetic sensor located on the (upper) medial aspect of the heel of a right (first) shoe in order to activate the foot-pressure power switch during control of a remote controlled bipolar coagulator system, according to one embodiment of the invention.

FIG. 7B shows the relative positions of right and left feet of an operator during activation of power switch 10 of a remote controlled bipolar coagulator system. In particular, the heel of (left) shoe 21 which bears magnetic unit 22 (not shown) has been moved in close proximity to the upper part of the medial aspect of the heel of (right) shoe 20 at the approximate location of second magnetic detector 38, in order to activate power switch 10.

Figure 7C:
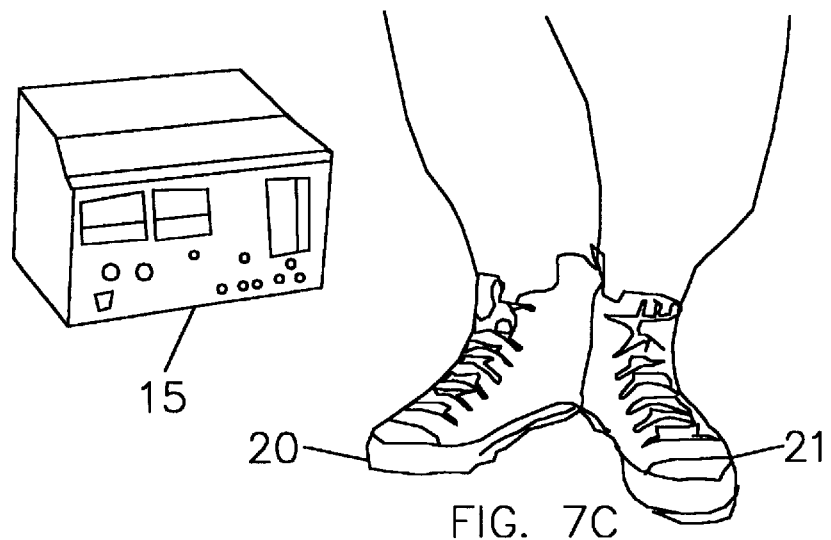
FIG. 7C shows the proximity of the heel of a left (second) shoe, which bears a magnet, to a first magnetic sensor located on the (lower) medial aspect of the heel of a right (first) shoe in order to deactivate the foot-pressure power switch during control of a remote controlled bipolar coagulator system, according to one embodiment of the invention.

FIG. 7C shows the relative positions of right and left feet of an operator during deactivation of power switch 10 of a remote controlled bipolar coagulator system. In particular, the heel of (left) shoe 21 which bears magnetic unit 22 (not shown) has been moved in close proximity to the lower part of the medial aspect of the heel of (right) shoe 20 at the approximate location of first magnetic detector 28, in order to deactivate power switch 10.

Figure 8:
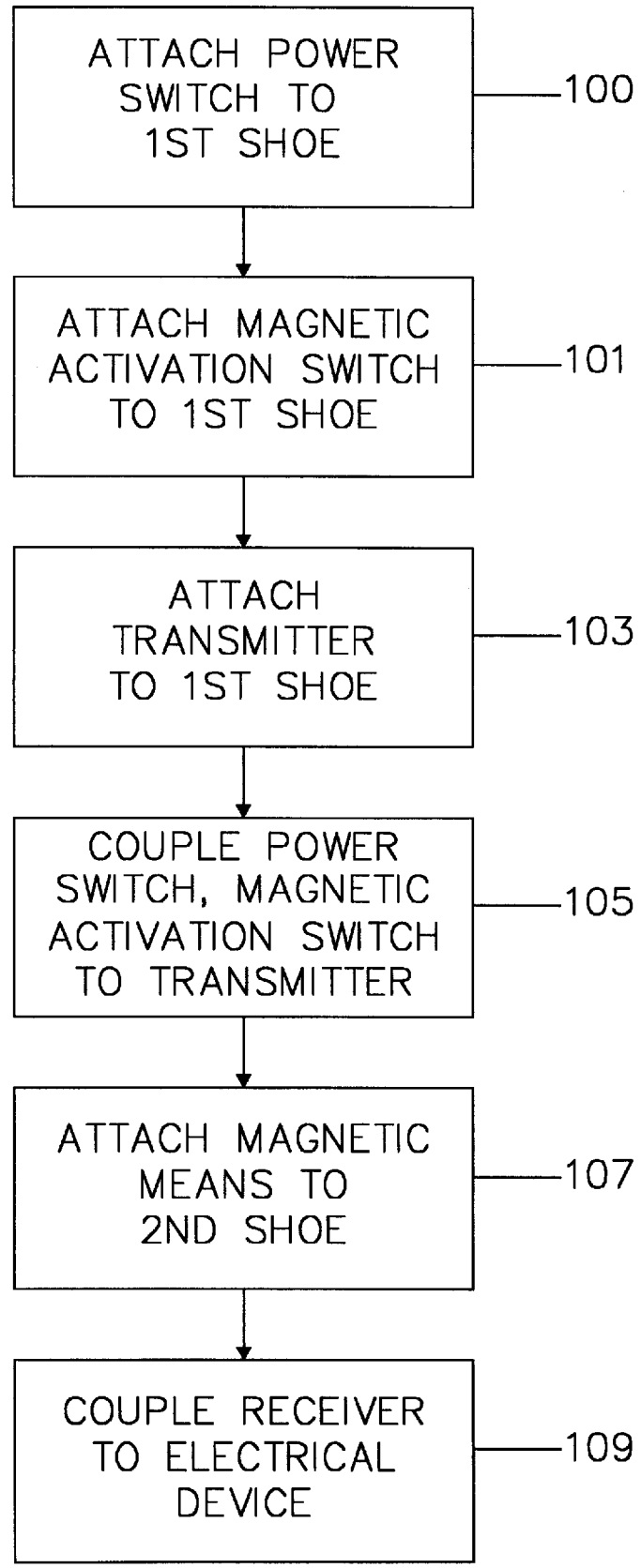
FIG. 8 is a schematic representation of steps involved in a method of making a remote controlled system including an electrically powered device according to one embodiment of the invention.

FIG. 8 schematically shows a series of steps showing a method of making a remote controlled system which includes an electrically powered device; in which a power switch is attached to a first shoe to be worn by an operator of the remote controlled system, in step 100; a magnetic activation switch is attached to the first shoe to be worn by the operator of the remote controlled system, in step 101; a transmitter for transmitting electromagnetic radiation is attached to the first shoe to be worn by the operator of the remote controlled system, in step 103; the power switch, the magnetic activation switch, and the transmitter are electrically coupled to each other, in step 105; a magnetic means is attached to a second shoe to be worn by an operator of the remote controlled system, in step 107; and a receiver for receiving electromagnetic radiation is coupled to the electrically powered device, in step 109.

According to a preferred embodiment of the invention, the method of making a remote controlled system including an electrically powered device includes a method of making a remote controlled system including a surgical instrument.

According to a more preferred embodiment of the invention the method of making a remote controlled system including an electrically powered device includes a method of making a remote controlled bipolar coagulator system, and the steps 100, 101, and 103 jointly comprise attaching a power switch, a magnetic activation switch, and a transmitter to a first shoe to be worn by an operator of the bipolar coagulator to provide a first shoe substantially as depicted for shoe 20 of FIG. 3; and the step 105 comprises electrically coupling the power switch, the magnetic activation switch, and the transmitter substantially as depicted for shoe 20 of FIG. 3; and the step 107 comprises attaching a permanent magnet to the second shoe to be worn by the operator of the bipolar coagulator to provide a shoe substantially as depicted for shoe 21 of FIG. 3.

Preferably the step 109 of the method of making a remote controlled bipolar coagulator system comprises coupling a receiver for receiving electromagnetic radiation to a coagulator control box of the remote controlled bipolar coagulator system in such a manner that electrical power is supplied to the coagulator control box when the receiver receives electromagnetic radiation of a pre-defined wavelength or wavelength range.

According to one embodiment of a method of making a remote controlled bipolar coagulator system, the step 100 may comprise attaching a power switch to the sole of a first shoe to be worn by an operator of the remote controlled bipolar coagulator system; the step 101 may comprise attaching a magnetic activation switch, comprising first and second magnetic detectors, to the heel area of the first shoe to be worn by an operator of the remote controlled bipolar coagulator system. Preferably the step 101 comprises attaching the first and second magnetic detectors to the medial aspect of the heel of the first shoe to be worn by an operator of the remote controlled bipolar coagulator system. The step 107 preferably comprises attaching a permanent magnet to the medial aspect of the heel of the second shoe to be worn by an operator of the remote controlled bipolar coagulator system.

By way of illustration, a prototype of a remote controlled bipolar coagulator system and method of making the same, according to the invention, will be described below. A foot-pressure power switch (Tape Switch Corp. of America, Farmingdale, N.Y.), two magnetic detectors (Diodes, Inc., Hall Effect Sensor IC, purchased from digi-key, part No. HAL104ND) and a radiofrequency transmitter (Visonic Ltd., Tel Aviv, Israel) were attached to a right shoe (canvas high-top basketball shoes, Converse, Inc., Reading, Mass.) and electrically coupled, substantially as depicted for shoe 20 of FIG. 3. A permanent magnet was secured to the medial aspect of the left shoe, substantially as shown for shoe 21 of FIG. 3. A laboratory version bipolar coagulator (Radionics, Burlington, Mass.) including a bipolar coagulator control box, was modified in such a manner that the on/off power input from the standard or conventional foot pedal was replaced by a radiofrequency receiver (Visonic Ltd., Tel Aviv, Israel).

The prototype described above was tested in the laboratory for ease of use and reliability, and was found to be fully functional during mimicking a wide range of positions and movements used during surgical procedures. Further, there was no noticeable difference in surgeon comfort and maneuverability between the standard basketball shoes and those modified for the prototype remote controlled bipolar coagulator system. While in the active state, the foot-pressure switch of the prototype was switchable between the on mode and the off mode by the application of relatively light pressure from the sole of the right shoe. The movements of the foot required to actuate the foot-pressure switch are ergonomically similar to those used to depress an optimally positioned foot pedal of prior art bipolar coagulators.

Foot movements were reliably used to bring the magnet of the left shoe in close proximity to one or the other of the two magnetic detectors in order to interchange the foot-pressure switch between the active and inactive states. Radiofrequency signals transmitted from the transmitter on the right shoe were successfully received by the receiver connected to the bipolar control box from all locations tested within a 6 feet radius of the receiver.

In the case of radiofrequency radiation transmitted from the transmitter located on the right shoe, possible interference with signal transmission between the transmitter and the receiver caused by radiofrequency output from the bipolar coagulator can be mitigated or eliminated by the use of electronic shielding techniques.

In a second prototype of a remote controlled bipolar coagulator system, an infrared signal transmitter and receiver system replaced the radiofrequency transmitter and radiofrequency receiver components of the first described prototype. In the case of the second prototype comprising an infrared signal transmitter and receiver system, signal transmission from the transmitter of the right shoe to the receiver of the bipolar coagulator control box was comparable to that for radiofrequency transmission as described above, while the possibility of radiofrequency interference from the bipolar coagulator control box was eliminated.

As an example of the usefulness of a remote controlled coagulator system according to the instant invention, during endoscopic procedures the remote control power switch of the system allows the surgeon to control coagulation functions while the surgeon's hands are engaged in controlling the endoscope, and in addition, allows the surgeon to freely change positions as dictated by the surgical procedure while retaining convenient access to the coagulator power switch at all times.

Whereas the remote control system has been disclosed with particular reference to a surgical coagulator, it is to be understood that the remote control system of the instant invention may similarly be used for the control of other surgical instruments, and electrically powered devices in general, in situations where hands-free control of the instrument or device by the operator and the freedom of mobility of the operator in spatial relationship to the instrument or device is either desired or necessary.

Thus, the remote control system and methods disclosed herein are applicable to electrically powered medical devices other than a surgical coagulator, such as a fluoroscope. For example, the foot-operated remote control system of the instant invention may be used to advantage in conjunction with a fluoroscope during interventional neuroradiology procedures, during which the surgeon's hands are occupied and a fluoroscope pedal is not always readily accessible. Similarly, the disclosed remote control system may also be used to control irrigation during various surgical procedures.

The disclosed remote control system and methods are also applicable to electrically powered devices in general, for example various machine tools in industrial applications. In this latter situation, in which an operator of a machine tool may be using both hands to position a workpiece in relation to the machine tool, a remote control power switch attached to the sole of a shoe worn by the operator may be much more convenient and effective than a foot pedal switch which is tethered to a length of electrical cable.

The foregoing embodiments are merely exemplary and are not to be construed as limiting the present invention. The present scheme can be readily applied to other types of apparatuses. The description of the present invention is intended to be illustrative, and not to limit the scope of the claims. Many alternatives, modifications, and variations will be apparent to those skilled in the art.

What is claimed is:

1. A remote control system for remotely controlling supply of electrical power to an electrically powered device by an operator, comprising:

transmitter which transmits electromagnetic radiation;

receiver which receives electromagnetic radiation;

first switch configured such that the operator can operate said first switch without the use of his hands; and second switch configured such that the operator can operate said second switch without the use of his hands, wherein said second switch switches said first switch between a first active state and second inactive state.

2. The remote control system as claimed in claim 1, wherein said first switch controls a supply of electrical power to the device.

3. The remote control system as claimed in claim 1, wherein said transmitter which transmits said electromagnetic radiation transmits either infrared radiation or radiofrequency radiation, and said receiver which receives said electromagnetic radiation receives either infrared radiation or radiofrequency radiation.

4. The remote control system as claimed in claim 1, wherein said first switch controls the supply of electrical power to a machine tool.

5. The remote control system as claimed in claim 1, wherein said first switch controls the supply of electrical power to a machine tool.

6. A remote control system for remotely controlling supply of electrical power to an electrically powered device by an operator, comprising:

transmitter which transmits electromagnetic radiation;

receiver which receives electromagnetic radiation;

foot-pressure power switch attached to a first shoe to be worn by the operator; and second switch attached to the first show to be worn by the operator.

7. The remote control system as claimed in claim 6, wherein said foot-pressure power switch is attached to a first shoe to be worn by the operator.

8. A remote control system for remotely controlling supply of electrical power to an electrically powered device by an operator, comprising:

transmitter which transmits electromagnetic radiation;

receiver which receives electromagnetic radiation;

first switch attached to a first shoe to be worn by the operator; and second switch attached to the first shoe to be worn by the operator, wherein said second switch switches said first switch between a first active state and a second inactive state.

9. A remote control system for remotely controlling supply of electrical power to an electrically powered device by an operator, comprising:

transmitter which transmits electromagnetic radiation;

receiver which receives electromagnetic radiation;

first switch attached to a first shoe to be worn by the operator; and a magnetic activation switch.

10. The remote control system as claimed in claim 9, wherein said magnetic activation switch comprises first and second magnetic detectors, said first and second magnetic detectors attached at separate locations to the operator.

11. The remote control system as claimed in claim 10, wherein said first and second magnetic detectors are separated by a distance ranging from 0.5 to 15 cm.

12. The remote control system as claimed in claim 9, wherein said magnetic activation switch is activated by a magnet, said magnet attached to a second shoe to be worn by the operator.

13. A remote controlled coagulator system including a bipolar coagulator for use by a surgeon in performing surgical procedures, said remote controlled coagulator system comprising:

a coagulator control box coupled to a supply of electrical power;

a receiving unit for receiving electromagnetic radiation;

a transmitting unit for transmitting electromagnetic radiation;

a first switching unit; and a second switching unit, wherein said transmitting unit, said first switching unit, and said second switching unit are mobile and unattached to both said coagulator control box and to said bipolar coagulator.

14. The remote controlled coagulator system as claimed in claim 13, wherein said transmitting unit, said first switching unit, and said second switching unit are attached to a first shoe to be worn by the surgeon.

15. The remote controlled coagulator system as claimed in claim 13, wherein said first switching unit comprises a power switch for turning on and turning off said supply of electrical power to said coagulator control box.

16. The remote controlled coagulator system as claimed in claim 13, wherein said second switching unit comprises a magnetic activation switch.

17. The remote controlled coagulator system as claimed in claim 13, wherein said first switching unit comprises a foot-pressure power switch attached to the sole of a first shoe to be worn by the surgeon.

18. The remote controlled coagulator system as claimed in claim 13, wherein said second switching unit comprises first and second magnetic detectors, said first and second magnetic detectors arranged on a first shoe to be worn by the surgeon.

19. The remote controlled coagulator system as claimed in claim 13, wherein said second switching unit comprises first and second magnetic detectors, said first and second magnetic detectors arranged along the medial aspect of the heel area of a first shoe to be worn by the surgeon.

20. The remote controlled coagulator system as claimed in claim 13, wherein said second switching unit comprises first and second magnetic detectors, wherein said first and second magnetic detectors are arranged on a first shoe to be worn by the surgeon, and said first and second magnetic detectors are separated by a distance ranging from 0.5 cm. to 15 cm.

21. The remote controlled coagulator system as claimed in claim 13, wherein said transmitting unit for transmitting electromagnetic radiation transmits one of infrared radiation and radiofrequency radiation, and said receiving unit for receiving electromagnetic radiation receives one of infrared radiation and radiofrequency radiation.

22. A remote controlled bipolar coagulator system including a bipolar coagulator and a bipolar coagulator control box, said remote controlled bipolar coagulator system comprising:

at least one electrode;

a mobile transmitter for transmitting electromagnetic radiation, wherein said mobile transmitter has an ON state and an OFF state, and said mobile transmitter is unattached and untethered to both said bipolar coagulator and to said bipolar coagulator control box; and a receiver for receiving said electromagnetic radiation, said receiver coupled to said bipolar coagulator control box.

23. The remote controlled bipolar coagulator system as claimed in claim 22, further comprising a first switching unit and a second switching unit, wherein said second switching unit switches said first switching unit between a first active state and a second inactive state, and wherein said first switching unit switches said mobile transmitter between said ON state and said OFF state when said first switching unit is in said first active state, but said first switching unit does not switch said mobile transmitter between said ON state and said OFF state when said first switching unit is in said second inactive state.

24. The remote controlled bipolar coagulator system as claimed in claim 23, wherein said first switching unit comprises a power switch and said second switching unit comprises a magnetic activation switch.

25. The remote controlled bipolar coagulator system as claimed in claim 23, wherein said first switching unit is attached to a first shoe to be worn by a person operating the remote controlled bipolar coagulator system.

26. The remote controlled bipolar coagulator system as claimed in claim 23, wherein said second switching unit comprises first and second magnetic detectors, said first and second magnetic detectors attached to a first shoe to be worn by a person operating the remote controlled bipolar coagulator system, and wherein said second switching unit is actuated by a magnetic unit, said magnetic unit attached to a second shoe to be worn by a person operating the remote controlled bipolar coagulator system.

27. A method for controlling the supply of electrical power to an electrically powered device, comprising the steps of:
   a) moving a magnetic unit in close proximity to a second magnetic detector of a magnetic activation switch so that a power switch is changed from an inactive state to an active state, wherein the power switch in the active state is switchable between an off mode and an on mode by the application of foot pressure to the power switch;
   b) applying foot pressure to the power switch so that the power switch is switched to the on mode, wherein when the power switch is in the on mode a transmitter for transmitting electromagnetic radiation transmits electromagnetic radiation.

28. The method for controlling the supply of electrical power to an electrically powered device as claimed in claim 27, further comprising the step of:
   c) after said step b), reapplying foot pressure to the power switch so that the power switch is switched to the off mode, wherein when the power switch is in the off mode a transmitter for transmitting electromagnetic radiation does not transmit electromagnetic radiation.

29. The method for controlling the supply of electrical power to an electrically powered device as claimed in claim 28, further comprising the step of:
   d) after said step c), moving the magnetic unit in close proximity to a first magnetic detector of the magnetic activation switch, so that the power switch is changed from the active state to the inactive state, wherein the power switch in the inactive state is not switchable between an off mode and an on mode by the application of foot pressure to the power switch.

30. The method for controlling the supply of electrical power to an electrically powered device as claimed in claim 29, further comprising the step of:
   e) after said steps a) through d), repeating steps a) through d) as many times as is necessary.

31. A method of turning on or turning off electrical power to an electrically powered device, comprising the steps of:
   a) first, moving a magnetic unit in close proximity to a second magnetic detector so that a power switch is changed from an inactive state to an active state;
   b) then after said step a), applying foot pressure to the power switch so that the power switch is switched to the on mode;
   c) after a requisite period of time, reapplying foot pressure to the power switch so that the power switch is switched to the off mode; and thereafter
   d) moving the magnetic unit in close proximity to a first magnetic detector so that the power switch is changed from the active state to the inactive state.

32. The method according to claim 31, further comprising the step of repeating said steps a) through d), as appropriate.

33. The method of claim 31, wherein applying foot pressure to the power switch of said step b) causes infrared radiation to be transmitted from an infrared transmitter, the infrared radiation is received by an infrared receiver, and the infrared radiation received by the infrared receiver causes electrical power to be turned on to the electrically powered device.

34. A method for controlling a bipolar coagulator during a surgical procedure using a remote control system, said method comprising the steps of:
   a) first, moving a magnetic unit in close proximity to a second magnetic detector so that a power switch is changed from an inactive state to an active state;
   b) then, applying foot pressure to the power switch so that the power switch is switched to an on mode;
   c) thereafter, operating the bipolar coagulator for a period of time commensurate with the surgical procedure;
   d) thereafter, reapplying foot pressure to the power switch so that the power switch is switched to the off mode; and
   e) thereafter, moving the magnetic unit in close proximity to a first magnetic detector so that the power switch is changed from the active state to the inactive state.

35. The method for controlling a bipolar coagulator as claimed in claim 34, further comprising the step of: after said step e), repeating steps a) through e) as deemed appropriate commensurate with the surgical procedure.

36. A method of making a remote controlled system including an electrically powered device, said method comprising the steps of:
   a) attaching a power switch to a first shoe to be worn by an operator of the electrically powered device;
   b) further attaching a magnetic activation switch to the first shoe to be worn by the operator of the electrically powered device;
   c) further attaching a transmitter to the first shoe to be worn by the operator of the electrically powered device, said transmitter for transmitting electromagnetic radiation;
   d) electrically coupling the power switch, the magnetic activation switch, and the transmitter;
   e) attaching a magnetic unit to a second shoe to be worn by the operator of the electrically powered device; and
   f) coupling a receiver to the electrically powered device, said receiver for receiving said electromagnetic radiation.

37. The method of making a remote controlled system including an electrically powered device as claimed in claim 36, wherein said step a) comprises attaching the power switch to the sole of the first shoe to be worn by the operator of the electrically powered device.

38. The method of making a remote controlled system including an electrically powered device as claimed in claim 36, wherein said step b) comprises attaching a magnetic activation switch having first and second magnetic detectors to the medial aspect of the heel of the first shoe to be worn by the operator of the electrically powered device.

39. The method of making a remote controlled system including an electrically powered device as claimed in claim 36, wherein said step c) comprises attaching a transmitter for transmitting one of infrared radiation and radiofrequency radiation to the first shoe to be worn by the operator of the electrically powered device.

40. The method of making a remote controlled system including an electrically powered device as claimed in claim 36, wherein said step e) comprises attaching a permanent magnet to the second shoe to be worn by the operator of the electrically powered device.

41. The method of making a remote controlled system including an electrically powered device as claimed in claim 36, wherein said step f) comprises coupling a receiver for receiving one of infrared radiation and radiofrequency radiation to the electrically powered device.

42. The method of making a remote controlled system including an electrically powered device as claimed in claim 36, wherein said step f) comprises coupling a receiver for receiving one of infrared radiation and radiofrequency radiation to a coagulator control box of a remote controlled bipolar coagulator system.

43. A remote control system for remotely controlling supply of electrical power to an electrically powered device by an operator, comprising:

infrared transmitter which transmits infrared radiation;

infrared receiver which receives infrared radiation;

first switch configured such that the operator can operate said first switch without the use of his hands; and second switch configured such that the operator can operate said second switch without the use of his hands, wherein said second switch switches said first switch between a first active state and a second inactive state.

44. The remote control system as claimed in claim 43, wherein supply of electrical power to said electrically powered device is turned on when said infrared receiver which receives infrared radiation from said infrared transmitter.

45. A remote control system for remotely controlling supply of electrical power to an electrically powered device by an operator, comprising infrared transmitter which transmits infrared radiation;

infrared receiver which receives infrared radiation;

first switch attached to a first shoe to be worn by the operator; and second switch attached to the first shoe to be worn by the operator;

wherein said first switch controls the supply of electrical power to a medical device.

46. The remote control system as claimed in claim 43, wherein said electrically powered device comprises a machine tool which is used in conjunction with a hand-held workpiece.

47. A remote control system for remotely controlling supply of electrical power to an electrically powered device by an operator, comprising:

infrared transmitter which transmits infrared radiation;

infrared receiver which receives infrared radiation;

first switch attached to a first shoe to be worn by the operator; and second switch attached to the first shoe to be worn by the operator;

wherein said first switch controls the supply of electrical power to a machine tool.

48. A remote control system for remote controlling supply of electrical power to an electrically powered device by an operator, comprising:

infrared transmitter which transmits infrared radiation;

infrared receiver which receives infrared radiation;

a foot-operated power switch attached to a first shoe to be worn by the operator; and a magnetic activation switch attached to the first shoe to be worn by the operator, wherein said magnetic activation switch comprises first and second magnetic detectors, and said magnetic activation switch switches said first switch between a first active state and a second inactive state.

49. A remote controlled coagulator system including a bipolar coagulator for use by a surgeon in performing surgical procedures, comprising:

a coagulator control box coupled to a supply of electrical power;

receiver which receives electromagnetic radiation;

transmitter which transmits electromagnetic radiation;

first switch; and second switch, wherein said transmitter, said first switch, and said second switch are mobile and unattached to both said coagulator control box and to said bipolar coagulator.

50. The remote controlled coagulator system as claimed in claim 49 wherein said transmitter, said first switch, and said second switch are attached to a first shoe to be worn by the surgeon.

51. The remote controlled coagulator system as claimed in claim 49 wherein said first switch comprises a power switch for turning on and turning off said supply of electrical power to said coagulator control box.

52. The remote controlled coagulator system as claimed in claim 49, wherein said second switch comprises a magnetic activation switch.

53. The remote controlled coagulator system as claimed in claim 49, wherein said first switch comprises a foot-pressure power switch attached to the sole of a first shoe.

54. The remote controlled coagulator system as claimed in claim 49, wherein said second switch comprises first and second magnetic detectors arranged on a first shoe.

55. The remote controlled coagulator system as claimed in claim 49, wherein said second switch comprises first and second magnetic detectors arranged along the medial aspect of the heel area of a first shoe.

56. The remote controlled coagulator system as claimed in claim 49, wherein said second switch comprises first and second magnetic detectors arranged on a first shoe, wherein said first and second magnetic detectors are separated by a distance ranging from 0.5 cm to 15 cm.

57. The remote controlled coagulator system as claimed in claim 49, wherein said transmitter which transmits electromagnetic radiation transmits one of infrared radiation and radiofrequency radiation, and said receiver which receives electromagnetic radiation receives one of infrared radiation and radiofrequency radiation.

* * * * *